(12) United States Patent
Seymour (10) Patent No.: US 10,052,476 B2
(45) Date of Patent: Aug. 21, 2018

(54) METHODS FOR FORMING AN ELECTRODE DEVICE WITH REDUCED IMPEDANCE

(71) Applicant: Neuronexus Technologies, Inc., Ann Arbor, MI (US)

(72) Inventor: John P. Seymour, Ann Arbor, MI (US)

(73) Assignee: NeuroNexus Technologies, Inc., Ann Arbor, MI (US)

( * ) Notice: Subject to any disclaimer, the term of this patent is extended or adjusted under 35 U.S.C. 154(b) by 14 days.

(21) Appl. No.: 14/941,784

(22) Filed: Nov. 16, 2015

(65) Prior Publication Data

US 2016/0067473 A1   Mar. 10, 2016

Related U.S. Application Data

(62) Division of application No. 13/617,355, filed on Sep. 14, 2012, now Pat. No. 9,192,757.

(60) Provisional application No. 61/534,787, filed on Sep. 14, 2011, provisional application No. 61/535,852, filed on Sep. 16, 2011.

(51) Int. Cl.
| | |
|---|---|
| *A61N 1/36* | (2006.01) |
| *A61N 1/04* | (2006.01) |
| *A61N 1/05* | (2006.01) |
| *A61B 5/04* | (2006.01) |
| *A61B 5/00* | (2006.01) |

(52) U.S. Cl.
CPC ............... *A61N 1/04* (2013.01); *A61B 5/04* (2013.01); *A61B 5/04001* (2013.01); *A61B 5/68* (2013.01); *A61N 1/05* (2013.01); *A61B 2562/0209* (2013.01); *A61B 2562/0285* (2013.01); *A61B 2562/125* (2013.01); *A61N 1/0534* (2013.01); *A61N 1/36* (2013.01)

(58) Field of Classification Search
USPC ............................... 427/2.1, 2.24, 98.4, 99.2
See application file for complete search history.

(56) References Cited

U.S. PATENT DOCUMENTS

| | | | | |
|---|---|---|---|---|
| 7,937,153 | B2 * | 5/2011 | Zhou ..................... | A61N 1/0543 607/54 |
| 8,636,884 | B2 | 1/2014 | Liu et al. | |
| 8,731,673 | B2 * | 5/2014 | Vetter .................. | A61N 1/0534 607/45 |
| 8,774,890 | B2 | 7/2014 | Ready et al. | |
| 8,886,279 | B2 | 11/2014 | Tathireddy et al. | |
| 9,192,757 | B2 * | 11/2015 | Seymour .................. | A61N 1/05 |

(Continued)

*Primary Examiner* — Brian K Talbot
(74) *Attorney, Agent, or Firm* — Haynes and Boone, LLP; J. Andrew Lowes (57) ABSTRACT

Improved low-cost, highly reliable methods for increasing the electrochemical surface area of neural electrodes are described. A mono-layer of polymeric nanospheres is first deposited on a metallization supported on a dielectric substrate. The nanospheres self-assemble into generally repeating lattice forms with interstitial space between them. Then, the geometric surface area of the metallization material is increased by either selectively etching part-way into its depth at the interstitial space between adjacent nanospheres. Another technique is to deposit addition metallization material into the interstitial space. The result is undulation surface features provided on the exposed surface of the metallization. This helps improve the electrochemical surface area when the treated metallizations are fabricated into electrodes.

16 Claims, 11 Drawing Sheets

(56) References Cited

U.S. PATENT DOCUMENTS

| | | | | |
|---|---|---|---|---|
| 2003/0195601 A1* | 10/2003 | Hung | .................... | A61N 1/0526 |
| | | | | 607/116 |
| 2011/0288391 A1 | 11/2011 | Rao et al. | | |
| 2012/0119760 A1* | 5/2012 | Pehrsson | ............. | H01L 29/0665 |
| | | | | 324/691 |
| 2013/0030275 A1* | 1/2013 | Seymour | ............ | A61B 5/04001 |
| | | | | 600/377 |
| 2013/0137082 A1* | 5/2013 | Park | ................... | G01N 27/3278 |
| | | | | 435/5 |
| 2013/0320273 A1* | 12/2013 | Kotov | ...................... | A61N 1/05 |
| | | | | 252/511 |
| 2014/0018639 A1* | 1/2014 | Jamieson | ........... | A61B 5/14735 |
| | | | | 600/301 |
| 2015/0112180 A1* | 4/2015 | Kim | .................... | A61B 5/0478 |
| | | | | 600/377 |
| 2016/0258070 A1* | 9/2016 | Kim | ......................... | C23F 1/44 |

\* cited by examiner

FIG. 7B fundamental unit for calculating area, equilateral triangle $D_s$ = diam of a sphere $d_m$ = height of deposition or the depth of etch $A_{equil}$ = area of equilateral triangle $A_{inc}$ = area increase either through etching or deposition $$A_{equil} = \frac{\sqrt{3}}{4}(D_s)^2$$

$$A_{inc} = \frac{\pi}{2} D_s d_m$$

$$A_{new\_total} = A_e + A_{inc} \times \frac{A_e}{A_{equil}}$$

$$\%A_{new\_ratio} = \left(1 + \frac{2\pi}{\sqrt{3}} \frac{d_m}{D_s}\right) \times 100$$

FIG. 8

Table 1. Estimating Change in Surface Area Assuming Hexagonal Packing

| Geometric Area of Electrode, um2 | Sphere Diam, um | #Triangles in Electrode | Area of Equal Triangle (Aequil), um2 | Perim of Three 60deg Sectors, um |
|---|---|---|---|---|
| 200 | 0.05 | 184,752 | 0.001 | 0.079 |
| 200 | 0.2 | 11,547 | 0.017 | 0.314 |
| 2000 | 1 | 4,619 | 0.433 | 1.571 |
| 2000 | 1 | 4,619 | 0.433 | 1.571 |
| 2000 | 0.2 | 115,470 | 0.017 | 0.314 |

| Depth of Etch or New Metal (dm), um | Area in One Dep Gap (Ainc), um2 | % Area Increase (A_new_ratio) |
|---|---|---|
| 0.02 | 0.002 | 263% |
| 0.09 | 0.028 | 263% |
| 0.45 | 0.707 | 263% |
| 1.00 | 1.571 | 463% |
| 1.00 | 0.314 | 1914% |

METHODS FOR FORMING AN ELECTRODE DEVICE WITH REDUCED IMPEDANCE

CROSS-REFERENCE TO RELATED APPLICATIONS

This application is a divisional of application Ser. No. 13/617,355, filed on Sep. 14, 2012, now U.S. Pat. No. 9,192,757, which claims priority from U.S. Provisional App. Ser. No. 61/534,787, filed on Sep. 14, 2011 and U.S. Provisional App. Ser. No. 61/535,852, filed on Sep. 16, 2011.

BACKGROUND OF THE INVENTION

1. Field of the Invention

This invention relates generally to the electrode field, and more specifically to new and useful methods for forming an electrode device with reduced impedance. Such electrode are useful when fabricated into neural electrode assemblies for electrically stimulating body tissue or for recording physiological conditions of the body tissue.

2. Description of Related Art

Ideally, conductive electrodes, such as electrodes for sensing and/or stimulation in neural probes, or other neural interface devices, have minimal impedance magnitude and impedance variance (e.g., for an electrode at different times). High impedance generally corresponds with several disadvantages. Sensing and recording electrodes with high impedance typically experience high thermal noise. Stimulation electrodes with high impedance require larger amounts of power during stimulation. Furthermore, a large amount of variance in impedance typically results in poor reliability and predictability during both sensing and stimulation modes of operation.

Increasing the geometric surface area or "footprint" of an electrode is one technique to reduce impedance magnitude and variance, but that approach reduces the electrode's spatial resolution. Increasing the electrochemical surface area of an electrode is another technique for reducing impedance magnitude and variance, but at significant cost and resources. Current methods, such as electrodeposition or electroplating, for increasing a neural electrode's electrochemical surface area are often performed post-process on individual devices after microfabrication and, therefore, are relatively expensive. Electrodeposition can also be performed in batch processes, but this usually has issues with uniformity and repeatability. Also, reliability issues, such as changes in the charge carrying capacity over time or delamination between the modified electrode material and the underlying substrate, can be a concern.

Thus, there is a need in the electrode field to create a new and useful method for reducing the impedance of a neural electrode device. The present invention provides such new and useful methods for manufacturing electrode device, particularly those that are adapted for use in neural interface applications.

SUMMARY OF THE INVENTION

The present invention relates to improved low-cost, highly reliable methods for increasing the electrochemical surface area of neural electrodes. In particular, the invention relates to the deposition of a mono-layer of polymeric nanospheres on a dielectric substrate. The nanospheres self-assemble into generally repeating lattice forms with interstitial space between them. In one embodiment, the metallization material that is left exposed between adjacent nanospheres is etched. Etching is only part-way through the thickness of the metallization. In another embodiment, metallization material that are suitable for subsequent use as an electrode in neural probes, and the like, are deposited on the dielectric substrate, filling in the interstitial space between the arrayed nanospheres. The deposited metallization material builds into pyramidal-type structures that are shaped by the size of the nanospheres and the interstitial spacing between them. The nanospheres are then removed leaving behind the shaped metallization deposits of relatively high surface area. Such metallization deposits help to minimize impedance magnitude and impedance variance from one electrode to the next.

A further improvement is to deposit alternating layers of metals into the interstitial space between the nanospheres. One of the metals, for example gold, is more readily etched than the other, for example platinum or iridium. The gold layers are then selectively etched to expose additional platinum surface area that was previously covered by the gold. This additional surface area is that which previously had gold both immediately above and below it.

BRIEF DESCRIPTION OF THE DRAWINGS

The present invention will be described by reference to the following drawings, in which like numerals refer to like elements, and in which.

The present invention will be described in connection with a preferred embodiments, however, it should be understood that there is no intent to limit the invention to the embodiment described. On the contrary, the intent is to cover all alternatives, modifications, and equivalents as may be included within the scope of the invention as defined by the appended claims.

DETAILED DESCRIPTION OF THE PREFERRED EMBODIMENTS

The present methods described herein are primarily referenced to forming a single electrode device, and in particular a neural electrode device. However, it should be understood that the present methods can be configured to form a plurality of electrode devices that are suitable for medical sensing or stimulation applications. In a preferred embodiment, the present methods can be adapted to manufacture an electrode that is suitable for any electrical stimulation technology and any recording or sensing technology having conductive electrodes, such as electrodes that are useful in physiological solutions. In that light, the methods described herein are readily adaptable to scaling to batch processes for forming a plurality of electrode devices with reduced impedance at relatively low cost and high uniformity from one electrode to the next.

Figure 1:
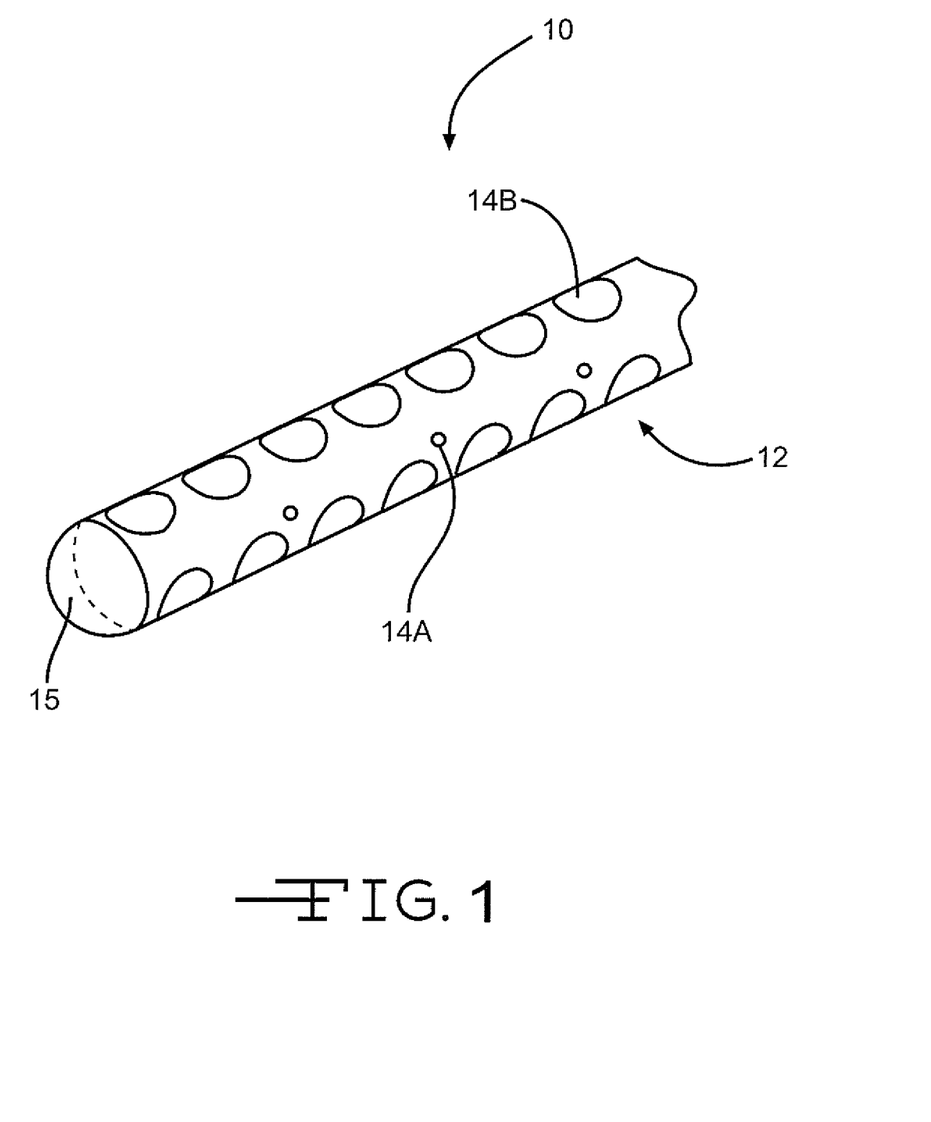
FIG. 1 is a perspective view of a neural interface system 10 according to the present invention.

Turning now to the drawings, FIG. 1 illustrates a neural interface system 10 according to the present invention. The neural interface system 10 comprises an electrode array 12 having a plurality of electrode sites 14A and 148. The electrodes may be adapted to optimally sample (record) 14A or selectively activate (stimulate) 14B neural populations and may be individually or simultaneously activatable to create an activation pattern. The neural interface system 10 may further include a pre-molded component 15 onto which the neural interface array is attached or assembled that supports the electrode array 12. The electrode array 12 is coupled to the pre-molded component 15 such that the electrodes 14A, 14B are arranged both circumferentially around and axially there along. Alternatively the electrode array 12 may be kept in its original planar form and attached to another planar component for mechanical support. The neural interface system 10 of the present invention is preferably designed for deep brain stimulation and, more specifically, for deep brain stimulation with fine electrode site positioning, selectivity, tunability, and precise activation patterning. The neural interface system 10, however, may be alternatively used in any suitable environment (such as the spinal cord, peripheral nerve, muscle, or any other suitable anatomical location) and for any suitable reason.

Methods for building the electrode array 12 comprising the electrodes 14A, 14B formed from shaped metallizations with reduced impedance will now be described.

Figure 2:
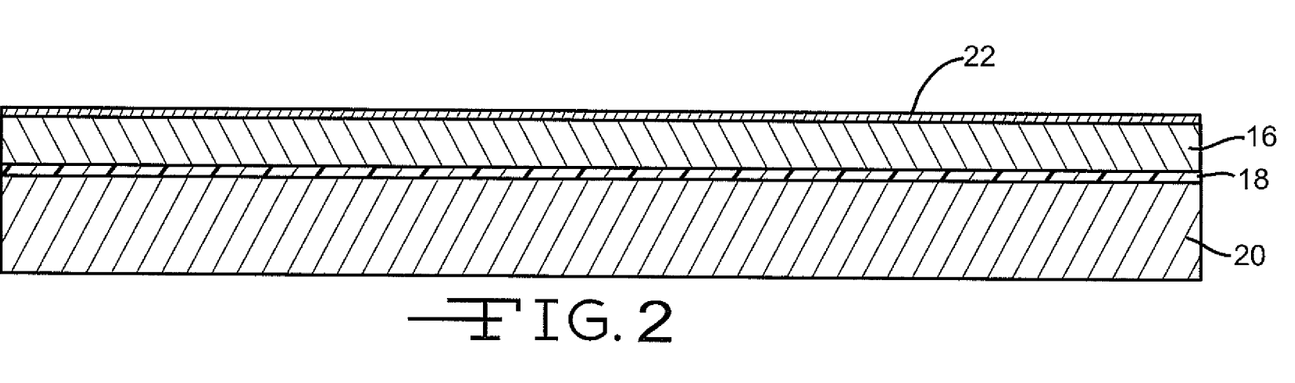
FIG. 2 is a schematic drawing showing a metallization layer 22 supported on a dielectric substrate 16 supported on a release layer 18 and a carrier layer 20 for forming an electrode 14A, 14B according to one embodiment of the present invention.

FIG. 2 shows the dielectric substrate 16 contacting a release layer 18 that is directly supported on a carrier 20. The dielectric layer 16 can be of a flexible thin material, preferably parylene, polyimide, silicone, or even a thin-film of silicon, or some combination of organic and inorganic dielectrics, but may alternatively be of any suitable material.

The carrier 20 is preferably made of glass or silicon, but may alternatively be made from any other suitable material. The carrier 20 may be flexible, rigid, or semi rigid depending on the microfabrication tooling (organic electronics equipment can increasingly use flexible substrates without a carrier layer such as in roll-to-roll manufacturing, whereas IC and MEMS microfabrication equipment use a rigid silicon carrier). A rigid carrier layer 20 has a height ranging from about 200 microns to about 925 microns, preferably greater than 500 microns.

A metallization layer 22 in FIG. 2 is deposited on the upper or outer surface 16A of the dielectric substrate 16. The metallization 22 is shown as a continuous layer and can be patterned using any suitable wet etch or dry etch wherein the mask is a photodefined resist or any other masking material patterned directly or indirectly using standard photolithography techniques having a perimeter extending from a lower metallization surface supported on the upper substrate surface 16A to an upper metallization surface spaced from the lower metallization surface by a height of the perimeter. The metallizations 22 can be deposited using any suitable thin film, semiconductor, microelectromechanical systems (MEMS) manufacturing technique or other microfabrication process, such as physical vapor deposition. Exemplary techniques and processes include evaporation and sputtering deposition. The metallizations layer 22 preferably includes a conductive material such as of gold (Au), platinum (Pt) or platinum-iridium, iridium oxide, titanium nitride, or any other metal, metal oxide, or conductive polymer having suitable electrically conductive properties.

Figure 3:
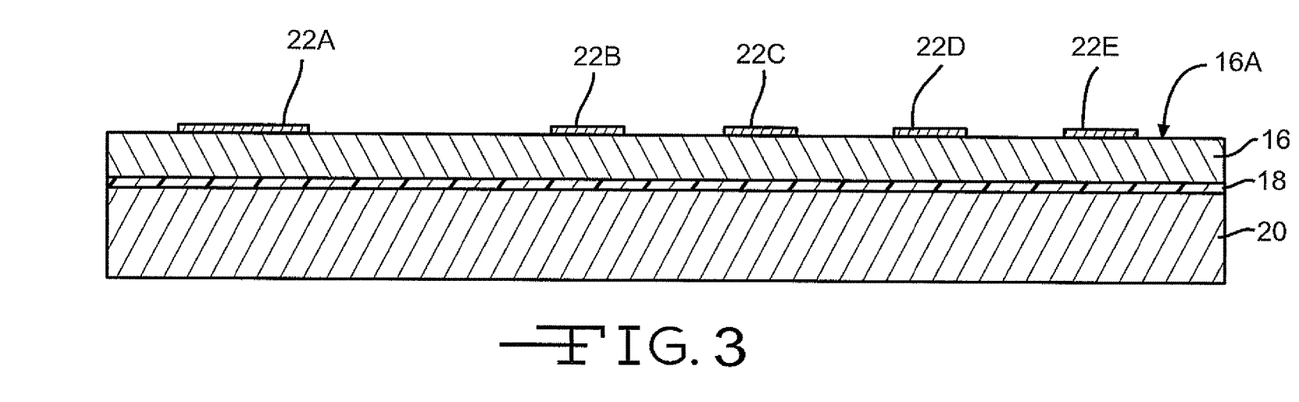
FIG. 3 is a schematic drawing showing a plurality of metallization layers 22A to 22E that are the result of etching the metallization layer 22 shown in FIG. 2A or after the mask layers 24A to 24F have been removed from FIG. 2C.

FIG. 3 shows where the continuous metallization 22 has been patterned into a plurality of discrete metallization structures 22A, 22B, 22C, 22D, 22E, etc. The metallization layer 22 can be patterned through etching, liftoff deposition (not shown), or any other suitable thin film, semiconductor manufacturing, MEMS manufacturing, or other microfabrication process.

Depending on the particular application for the finished neural interface system 10, the dielectric substrate 16, the release layer 18 and the carrier 20 can be flexible, semi-flexible, or rigid. The present method can further include patterning the metallization structures 22A, 22B, 22C, 22D, 22E, etc. to include conductive traces, bond pads, and other suitable conductive elements.

Figure 4:
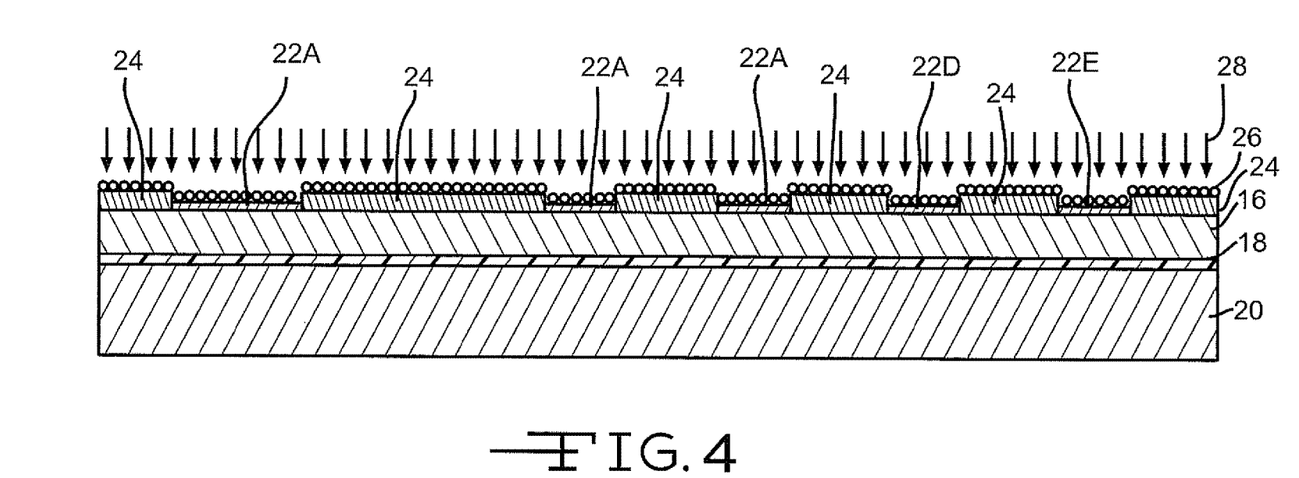
FIG. 4 is a schematic drawing showing deposition of a mono-layer of nanospheres 26 being deposited on the metallizations 22A to 22E of FIG. 3.

In FIG. 4, a layer of nanospheres 26 has been deposited onto the dielectric substrate 16 to cover both the shaped metallizations 22A, 22B, 22C, 22D, 22E, etc. and the substrate surface 16A between adjacent metallizations. The nanospheres 26 form a high-density, high-resolution spatial pattern serving as a substantially uniform mask or template over the surface of the individual metallizations. That is because the nanospheres 26 are substantially identical in size and shape. When they are deposited in a monolayer onto the metallizations 22A, 22B, 22C, 22D, 22E, etc., the nanospheres 26 self-assemble into a tightly packed, uniform pattern.

For example, the present method can include depositing a monolayer of nanospheres 26 onto the metallizations 22A, 22B, 220, 22D, 22E, etc. by drop wetting (direct application of the nanospheres in solution) and then allowing them to self-assemble into hexagonally packed patterns (FIG. 8) upon de-wetting. This embodiment includes depositing a nanosphere solution including nanospheres and a solvent onto the metallization structures 22A, 22B, 22C, 22D, 22E, etc. The solvent is then evaporated. The solvent is preferably selected based on its viscosity, evaporation rate, and wettability on the metallizations patterned on the dielectric substrate 16.

In one illustrative example, the solution includes polystyrene spheres mixed in a solvent of ethanol and de-ionized water. The ratio of ethanol to de-ionized water is approximately 4:1. However, the solution can include nanospheres 26 other than those of polystyrene, such as glass, and a suitable solvent other than a mixture of ethanol and de-ionized water. The solution is preferably dropped onto the dielectric substrate 16 such that a monolayer of nanospheres 26 is distributed substantially uniformly on the metallization structures 22A, 22B, 22C, 22D, 22E, etc.

Depositing the nanosphere solution may be performed by using the Langmuir-Blodgett technique to transfer a pre-fabricated monolayer of nanospheres 26 onto the metallizations 22A, 22B, 22C, 22D, 22E, etc. patterned on the dielectric substrate 16. In an example, nanospheres 26 having a surface tension of $\gamma_{-NS}$ are in a solvent having a surface tension of $\gamma$-solvent. It is given that $\gamma$-NS is less than $\gamma$-solvent. Then, a monolayer of nanospheres 26 forms at the exposed surface of metallizations 22A, 22B, 22C, 22D, 22E, etc. patterned on the dielectric substrate 16. The substrate 16 supported on the carrier 20 can be moved through the solution to transfer the monolayer of the nanospheres 26 thereto.

Illustratively, one can use the drop wetting method by mixing a nanosphere solution (e.g., 5% w/v solution) into a 4:1 volume mixture of ethanol to de-ionized water. When applied to a patterned dielectric substrate 16 at room temperature on a horizontal surface, the nanospheres 26 will self-assemble along a contact line during the evaporation or de-wetting process.

Evaporation of the solvent can occur unassisted or be accelerated with environmental changes, such as in temperature and pressure from that of an ambient atmosphere.

A second preferred embodiment is where the nanospheres 26 are deposited onto the metallization structures 22A, 22B, 22C, 22D, 22E, etc. via spin-coating the above described nanosphere solution. If desired, the nanosphere solution can have a different viscosity, wettability, or other mixture ratio than that used with the drop-wetting or Langmuir-Blodgett technique. Furthermore, depending on the nature of the nanosphere solution, spin-coating can include a particular rate of spinning and/or acceleration.

According to the present invention, a series of recessed undulations 22A', 22B', 22C', 22D', 22E', etc. or upstanding undulations 22A", 22B", 22C", 22D", 22E", etc. are formed on the surface of the metallizations 22A, 22B, 22C, 22D, 22E, etc. The recessed or upstanding undulations can be approximately pyramidal wave undulations, square wave undulations, approximately triangular wave undulations, or an undulation of any other suitable shape.

Figure 5:
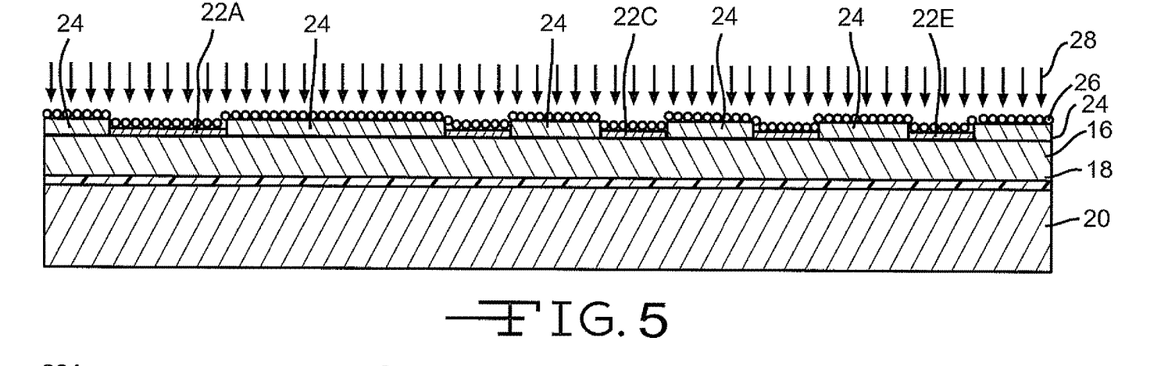
FIGS. 5, 5A and 5A' are schematic drawings showing a method according to the present invention where undulations are formed in the metallizations 22A to 22E by etching recesses 30 into their heights.
Figure 5A:
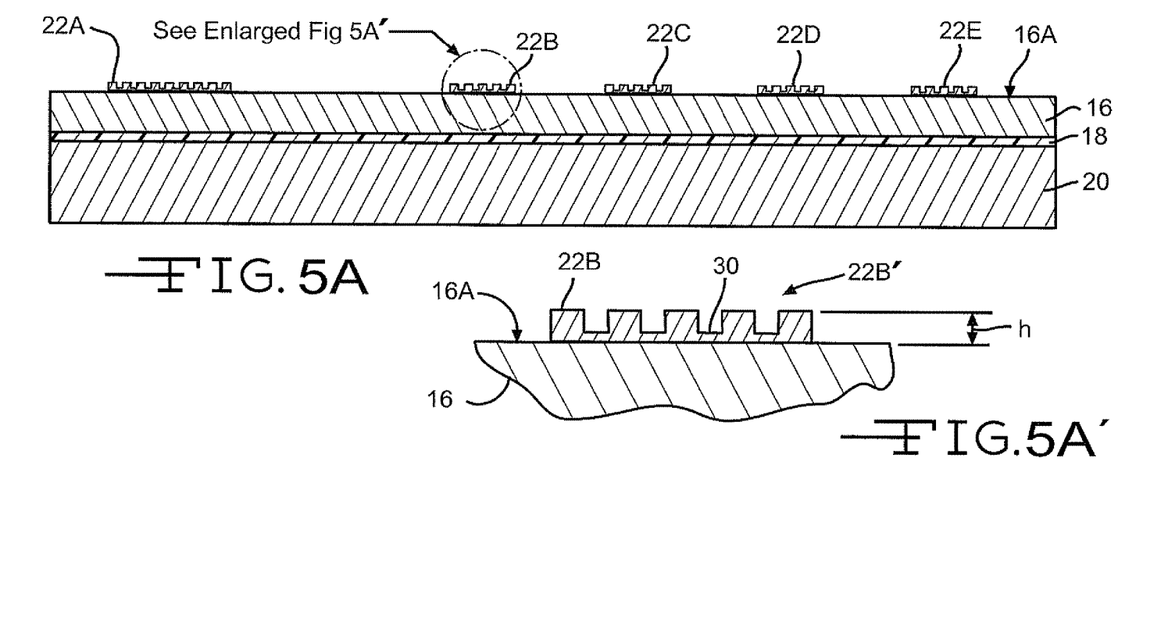

FIGS. 5, 5A and 5A' show recessed undulations 22A', 22B', 22C', 22D', 22E', etc. that have been formed by etching 28 recesses 30 into the height of the respective metallizations 22A, 22B, 22C, 22D, 22E, etc. Etching 28 the recesses 30 into the metallizations takes place beneath the interstitial spaces of the layer of assembled nanospheres 26. The result is undulations 22A", 22B", 22C", 22D", 22E", etc. comprising recesses extending into the original height (h) of the metallization layers supported on the substrate 16.

For etching, it is preferred that the nanospheres 26 have a diameter ranging from about 20 nanometer (nm) to about 1,000 nm. Etching can be performed with any suitable etching process. One advantage of etching is that it does not require any adhesion between the existing metallization layer and newly deposited conductive material. Platinum, for example, is a commonly used biocompatible metal that can be dry etched using techniques described in U.S. Pat. No. 6,323,132 with a reactive ion etcher. The contents of this patent are incorporated herein by reference.

In that manner, etching forms the recesses 30 having a depth extending part-way through the height of the metallization 22B from that portion of its upper surface of the metallization not contacted or otherwise covered by a nanosphere 26. The recesses 30 can extend from about 1% to about 99% into the height of the metallizations 22A, 22B, 22C, 22D, 22E, etc. More preferably, the recesses are from about 50% to about 90% into the original metallization height. The metallizations shown in FIG. 5A have a height measured from the upper surface 16A of the dielectric 18 to the upper surface of the as-deposited metallization of from about 0.25 micron to about 20 microns, more preferably from about 10 microns to about 20 microns.

Figure 6:
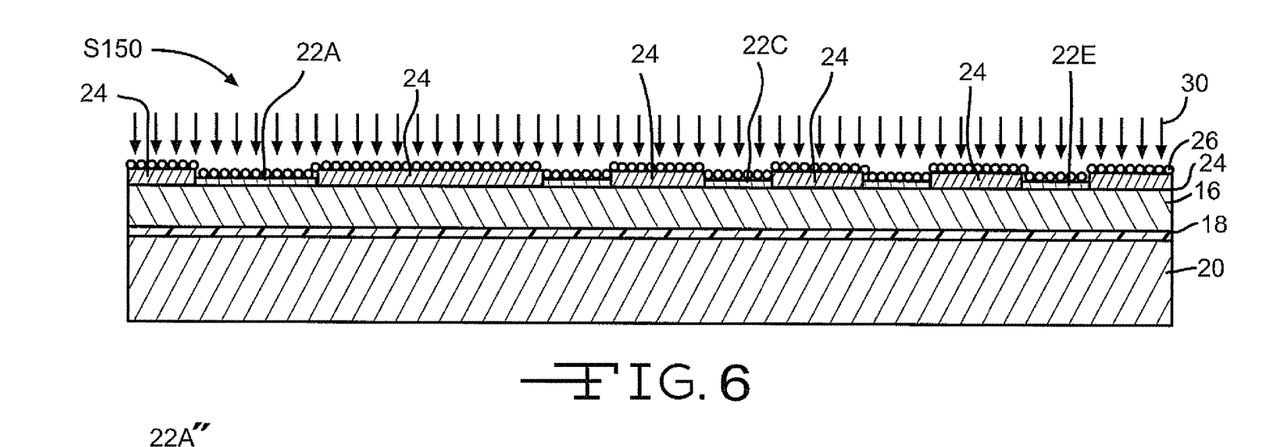
FIGS. 6, 6A and 6A' are schematic drawings showing a method according to the present invention where undulations are formed by depositing metallization material 32 onto the metallizations 22A to 22E.
Figure 6A:
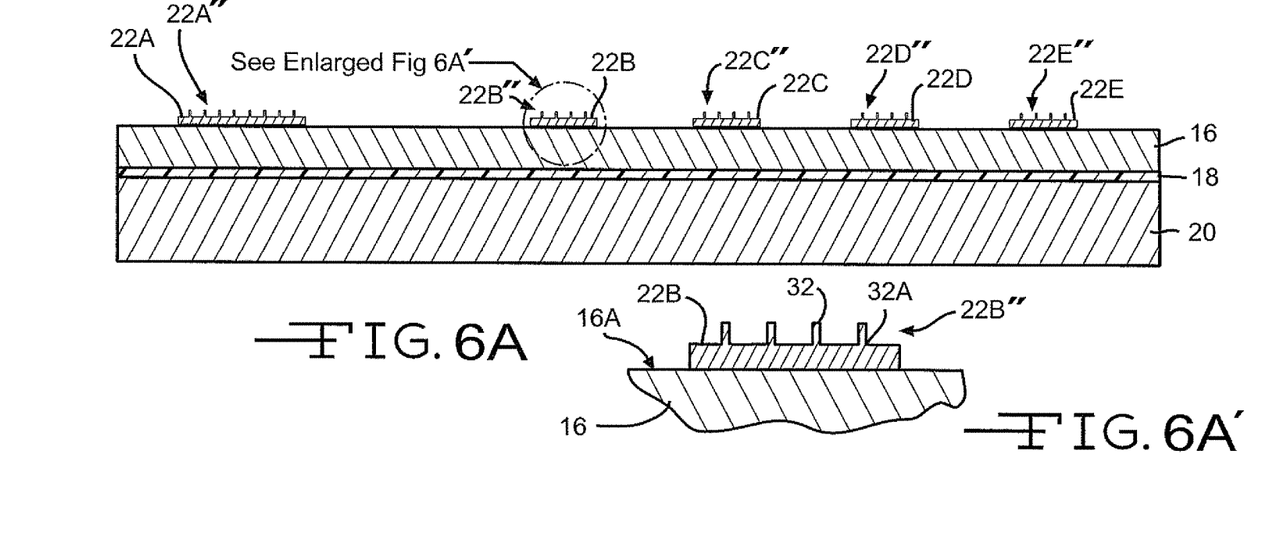

FIGS. 6, 6A and 6A' relate to an alternative method where the upstanding undulations 22A", 22B", 22C", 22D", 22E", etc. are formed by depositing 30 additional metallization material (e.g., in a lift-off deposition) onto the metallizations 22A, 22B, 22C, 22D, 22E, etc. through the interstitial spaces between the nanospheres 26. Deposition 30 continues until the desired height of the added metallization material 32 measured from its base 32A supported on the upper surface of the original metallization 22B is achieved. For this technique, it is preferred that that the nanospheres have a diameter ranging from about 500 nm to about 5,000 nm.

Figure 7A:
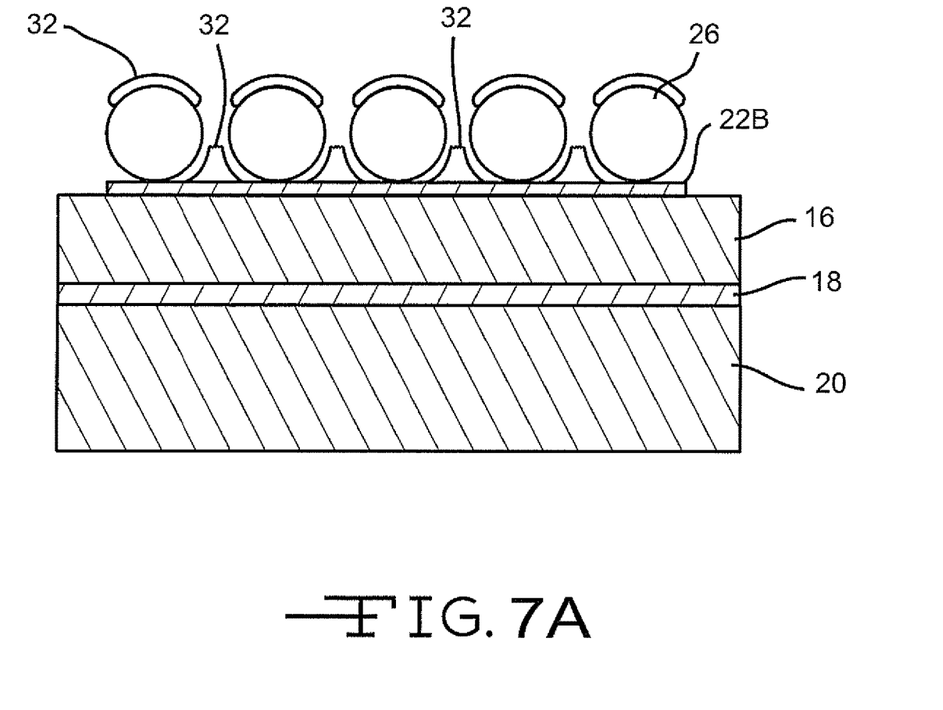
FIG. 7A is a schematic showing deposition of metallization material 32 between adjacent nanospheres 26.

One advantage of this variation is that depositing material preferably results in metal-metal bonds and predictable surface properties. FIG. 7A illustrates a representative one of the undulations where the additional metallization material 32 forms a base on the upper surface of the metallization 22B and build-up in a pyramidal manner. That is without contacting the adjacent nanospheres 26, but while following their generally circular contour. In that respect, the height of the upstanding undulations is preferably about 90% of the radius of the nanosphere. It has been discovered that this ratio provides maximum added surface area for the added metallization. That means the upstanding additional or secondary metallization material has a height ranging from about 225 nm to about 2,250 nm above the upper surface of the primary metallization 22.

Moreover, the added metallization does not grow so high as to prevent the subsequent removal of the nanospheres. In order for nanosphere removal, it is important that the added metallization not extend past the imaginary equator and over the upper half of the hemisphere. With this rule, it has been determined that approximately a four-fold increase in the geometric surface area (GSA) is achievable.

Figure 7B:
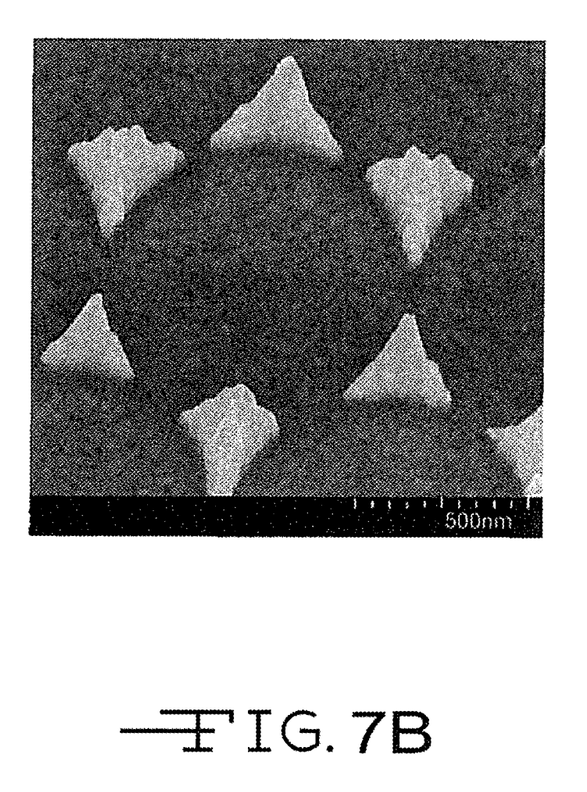
FIG. 7B is a partial photographic image of an exemplary electrode resulting from the method of the present invention depicted in FIGS. 6, 6A and 6A'.

FIG. 7B is a photograph showing how the deposited metallization material builds up from the upper surface of a metallization without contacting the nanospheres 26. The nanospheres 26 have been removed in the photograph, but the generally circular shape of one of them is delineated by the circle bordered by the deposited metallization material, which is seen as the off-white pyramidal bodies having somewhat triangular bases.

In both embodiments, the recessed undulations 22A', 22B', 22C', 22D', 22E', etc and extending 22A", 22B", 22C", 22D", 22E", etc on the respective metallizations are preferably bounded by the interstitial spaces of the nanospheres 26. Since the nanospheres 26 are substantially uniform in shape and arranged in a substantially uniform distribution in the layers of FIGS. 5 and 6 supported on the upper surface of the metallization 22A, 22B, 22C, 22D, 22E, etc., there is a substantially uniform distribution of interstitial spaces between the nanospheres 26. Consequently, the undulations 22A', 22B', 22C', 22D', 22E', etc. and 22A", 22B", 22O", 22D", 22E", etc. are substantially uniformly distributed throughout the surface area of the shaped metallization.

If desired, the nanospheres 26 are removed from the dielectric substrate 18 after forming recessed or extending the undulations 22A', 22B', 22C', 22D', 22E', etc. and 22A", 22B", 22O", 22O", 22E", etc. on the respective metallizations 22A, 22B, 22C, 22D, 22E, etc. or, the nanospheres 26 can be left on the metallizations.

The undulations 22A', 22B', 22C', 22D', 22E', etc and 22A", 22B", 22C", 22D", 22E", etc significantly increase the electrochemical surface area (ESA) of the electrode, particularly relative to the geometric surface area (GSA) of an electrode formed from one of the metallization according to the present invention. The interstitial spaces of the nanospheres (or "pores" of the layers of the nanospheres) are preferably arranged in a substantially uniform distribution, thereby enabling substantially uniform arrangement of the undulations.

The particular form of the undulation, whether they be of the recessed or the extending form (etching or deposition) of the metallizations depends on the functional application of the electrode that will be manufactured from the metallization device, desired dimensions of the electrode, extensions, and/or recesses, materials within the metallization, and/or any suitable factor. In any event, the undulating surface provides an increased ESA predicated on the diameter and packing arrangement of the nanospheres 26, and the depth of recess 30 for the recessed undulation 22A', 22B', 22C', 22D', 22E', etc. or the increased height of the deposited metallization material 32 for the extending undulations 22A", 22B", 22C", 22D", 22E", etc.

Figure 8:
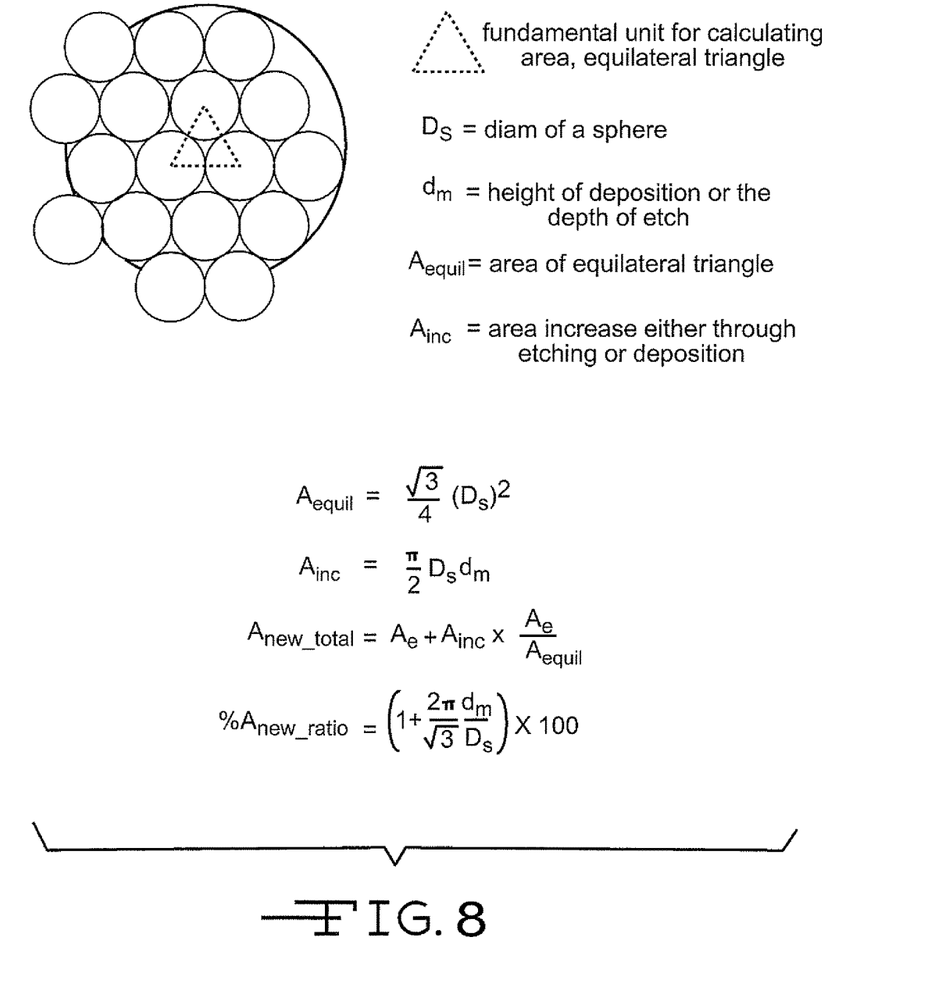
FIG. 8 is a schematic of nanosphere packing and calculation of increased electrochemical surface area resulting from the methods of the present invention.
Figure 9:
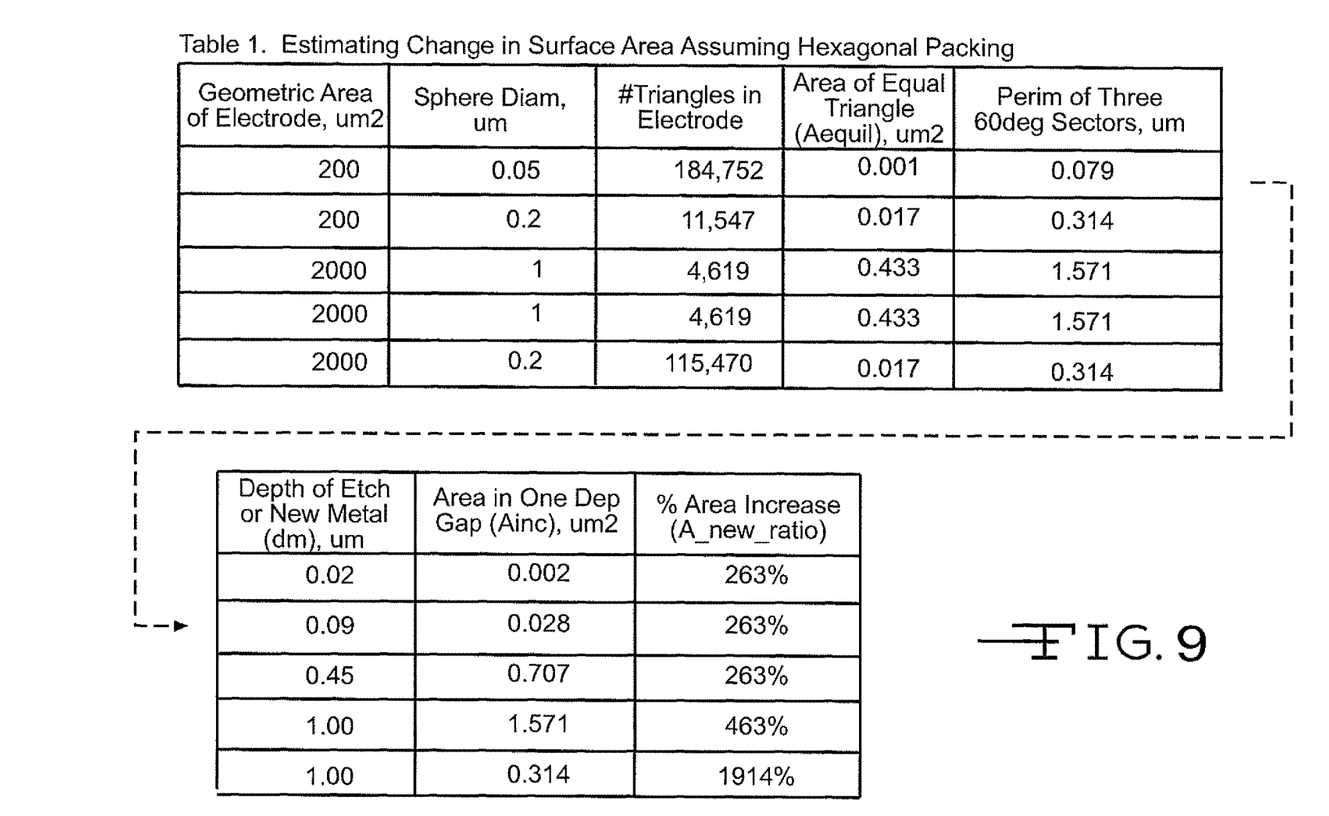
FIG. 9 is a table of results from one example of the method of the present invention.

As shown in FIG. 8, the amount that the ESA increases as is inversely proportional to the diameter of the sphere:

$$A_{equil} = \frac{\sqrt{3}}{4}D_s^2$$

$$A_{inc} = \frac{\pi}{2}D_s d_m$$

$$A_{new\_total} = A_e + A_{inc} \times \frac{A_e}{A_{equil}}$$

$$\% A_{new\_ratio} = \left(1 + \frac{2\pi}{\sqrt{3}}\frac{d_m}{D_s}\right) \times 100$$

where $A_{inc}$=additional area additional area created inside the fundamental unit of the equilateral triangle formed by 3 adjacent spheres when hexagonally packed, $D_s$=diameter of a sphere, $d_m$=height of deposition or the depth of etch, and $A_e$=geometric area of electrode (derived from the metallizations 22). Estimated area change in various illustrative examples of etched metallization electrode sites (FIGS. 5, 5A and 5A') are shown in Table 1 of FIG. 9.

In some preferred embodiments, the present invention methods additionally or alternatively include one or more of several variations described below.

Figure 10A:
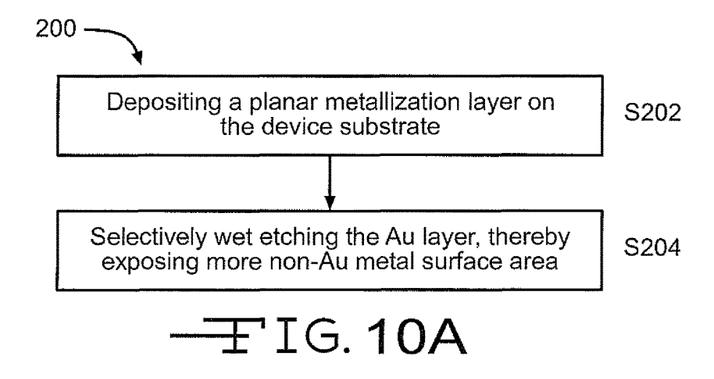
FIG. 10A are a flow chart of the steps used to increase the effective surface area of deposited platinum layers 40 by etching an intermediate gold layer 42.
Figure 10B:
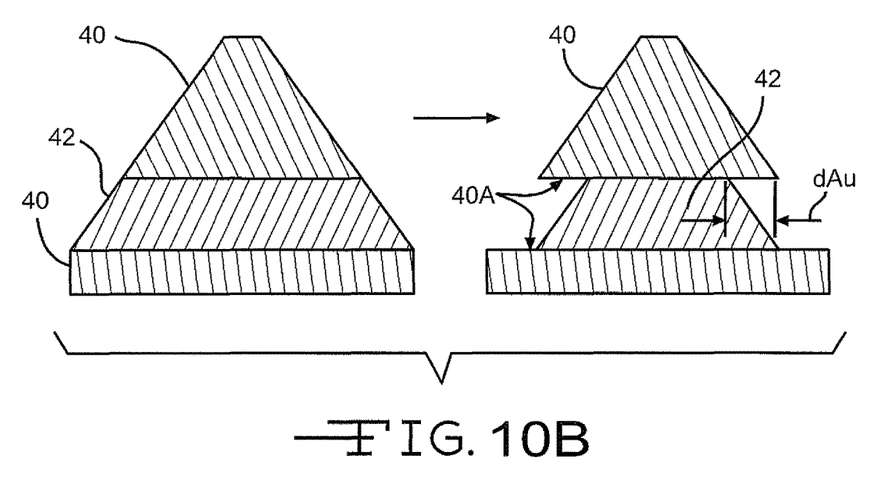
FIG. 10B is a schematic drawing showing the steps described in the flowchart of FIG. 10A.

As shown in FIGS. 10A and 10B, a further surface area increase can be achieved according to the present invention by undercutting one or more alternating layers of patterned metal. In one version of this embodiment, the method includes: depositing a planar metallization layer stack (e.g., Au/Pt, Au/Ir, or other Au stack) onto the dielectric substrate 16, and then selectively wet etching the Au metal.

An example of this is to deposit a layer of platinum 40 onto the dielectric layer (not shown in FIG. 10B) using one of the methods previously described with respect to FIGS. 3 and 4. Without removing the nanospheres 26, a layer of gold 42 is deposited on top of the platinum 40 followed by a second layer of platinum. The nanospheres 26 and the underlying photoresist pattern 24 are then removed and the gold 42 is wet etched. Etching serves to expose additional surface area of the platinum 40 that was previously positioned both above and below the gold. This is shown by the exposed surface 40A of the platinum layers 40 in FIG. 10B.

It is important to not etch too much of the gold 42 so that it can no longer act as a structural support for the platinum 40. In FIG. 10B, the depth of etch is depicted as $d_{Au}$, which is less than the original width of the gold layer measured parallel to the plane of the dielectric substrate 16. In addition to platinum, iridium, iridium oxide, and titanium nitride are suitable metallization materials for use with this gold etching process. In that manner, gold etching serves to expose more of the non-Au metal surface area.

Figure 11A:
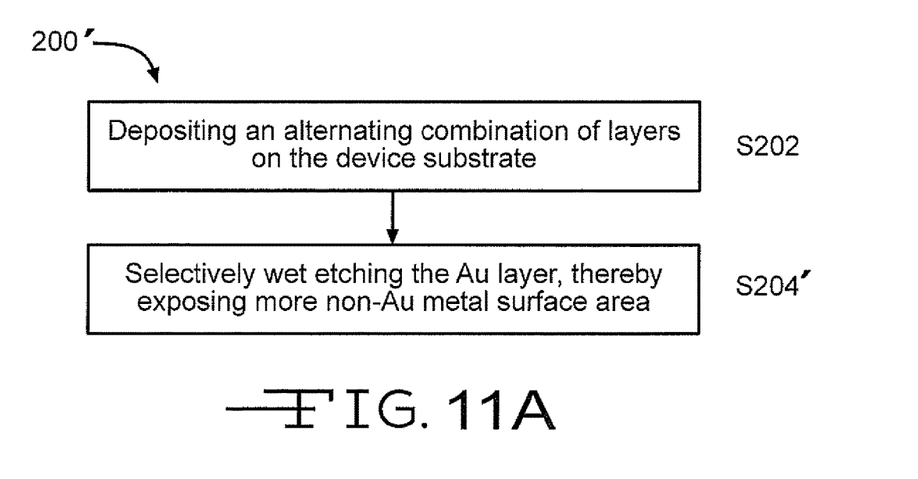
FIG. 11A are a flow chart of the steps used to increase the effective surface area of deposited platinum layers 40 by etching an intermediate gold layer 42 in a deposition profile of Pt/Au/Pt/Au/Pt.
Figure 11B:
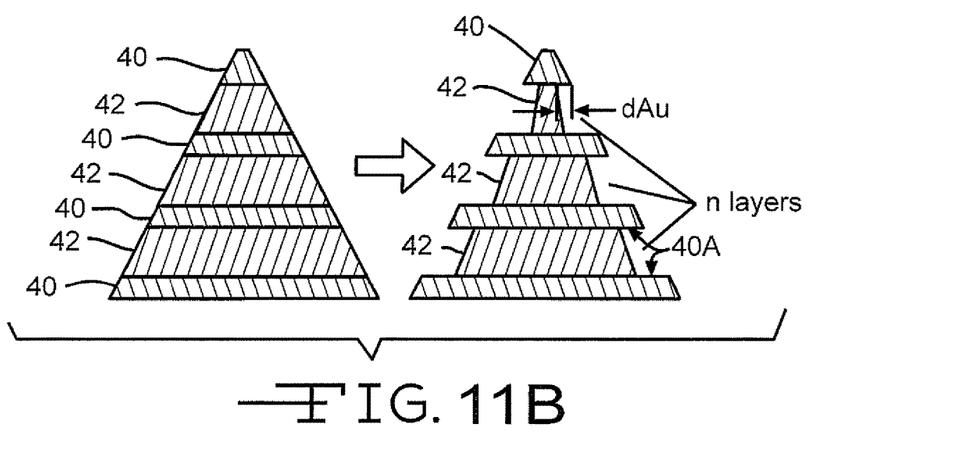
FIG. 11B is a schematic drawing showing the steps described in the flowchart of FIG. 11A.

FIGS. 11A and 11B relate to another embodiment of the method according to the present invention. This embodiment additionally or alternatively includes depositing an alternating combination of layers on the dielectric substrate (not shown in FIG. 11B). In one specific embodiment alternating layer of platinum 40 and gold 42 are deposited one on top of the other until a stack of a desired height is achieved. In a similar manner as described above with respect to FIGS. 10A and 10B, the gold layers are wet etched to undercut and expose addition platinum surface area. As described above, it is important not to etch too much of the gold 42. In FIG. 11B, the depth of etch is depicted as $d_{Au}$, which is less than the original width of the gold layer measured parallel to the plane of the dielectric substrate 16. Enough gold must be left to serve as a structural pillar supporting the above platinum and gold layers. An example of this embodiment is alternating layers of Au/Pt/Au/Pt/Au/Pt stacked one on top of the other. Gold etching preferably forms more ESA.

Although omitted for clarity, the preferred embodiments of the present methods include every combination and permutation of the various processes described above. Furthermore, the preferred embodiments of the present method can be executed by a computer program or other system including computer program code for controlling hardware (e.g., machines for deposition, sputtering) in an automated fashion.

Neural Interface Device with Reduced Impedance

As previously discussed with respect to FIG. 1, a neural interface device 10 with reduced impedance according to the present invention includes the dielectric substrate 16 supporting the electrode array 12 comprising the plurality of electrodes 14A, 14B. After the metallization material 22 has been provided with an undulating surface characteristic, whether the undulations are recessed or upstanding the neural array is further completed with the addition of top dielectric, bond pads if necessary, vias, and other desired features (none of these are shown here). Finally the neural array including the dielectric substrate 16 is removed from the carrier 20. The release layer 18 facilitates this separation in some cases but not always required especially if the dielectric substrate 16 only has weak bonding to the carrier 18. The dielectric substrates (top and bottom) and the electrode array 12 are then formed into a desired shape of the neural interface system 10, which can be either planar or three-dimensional such as the cylindrical shape shown. The neural interface device 10 can be a planar probe with the electrode array 12, a cylindrical probe with the electrode array, a substantially planar or curved substrate with the electrode array, or any suitable electrode device.

At least a portion of each electrode 14A, 14B has a substantially uniform undulating surface described above. At least a portion of the substantially uniform undulating surfaces of the electrodes 14A, 14B includes peaks and/or crevices (e.g., recesses) that are preferably distributed in a regular arrangement and, more preferably, in an approximately hexagonal arrangement as shown in FIGS. 5A, 5A', 6A and 6A'. The undulating surfaces increases the electrochemical surface area of the electrodes 14A, 14B, thereby reducing their impedance and improving their functionality for stimulation and sensing purposes.

While this invention has been described in conjunction with preferred embodiments thereof, it is evident that many alternatives, modifications, and variations will be apparent to those skilled in the art. Accordingly, the present invention is intended to embrace all such alternatives, modifications and variations that fall within the broad scope of the appended claims.

What is claimed is:

1. A method for providing a neural interface system, comprising the steps of:
    depositing at least one primary metallization layer supported on the substrate, the metallization layer having a thickness;
    depositing a monolayer of nanospheres contacting an upper surface of the primary metallization layer; and
    treating the upper surface of the primary metallization layer not covered by the nanospheres to thereby form a plurality of pyramidal structures the treating comprising depositing a secondary metallization layer on exposed portions of the primary metallization layer, thereby forming the plurality of pyramidal undulating structures, removing the nanospheres from the substrate and then configuring the substrate supporting the primary metallization layer with plurality of pyramidal structures for contact with body tissue as a component of a neural interface device.

2. The method of claim 1 wherein the substrate is a dielectric material selected from the group consisting of parylene, polyimide, silicone, silicon carbide, and silicon.

3. The method of claim 1 including selecting the primary metallization layer from the group consisting of gold, platinum, platinum/iridium alloy, iridium oxide, and titanium nitride.

4. The method of claim 1 wherein the thickness of the primary metallization layer ranges from about 10 microns to about 20 microns.

5. The method of claim 1 wherein the nanospheres are comprised of polystyrene or glass.

6. The method of claim 1 wherein the nanospheres have a diameter in a range from about 20 nm to about 1,000 nm.

7. The method of claim 1 wherein the nanospheres are of substantially identical size and shape.

8. The method of claim 1 including mixing the nanospheres with ethanol and de-ionized water to form a nanosphere solution that is deposited on the primary metallization layer.

9. A method for providing a neural interface system, comprising the steps of:
    depositing at least one primary metallization layer on a substrate, the primary metallization layer having a thickness;
    depositing a monolayer of nanospheres contacting an upper surface of the metallization layer; and
    treating the upper surface of the primary metallization layer not contacted by the nanospheres to form a plurality of pyramidal undulating structures, the treating comprising depositing a secondary metallization layer on exposed portions of the primary metallization layer, thereby forming the plurality of pyramidal undulating structures.

10. The method of claim 9 wherein the nanospheres have a diameter ranging from about 500 nm to about 5,000 nm.

11. The method of claim 9 wherein a second thickness of the secondary metallization layer is in a range from about 225 nm to about 2,250 nm above the upper surface of the primary metallization layer.

12. The method of claim 9 including discontinuing deposition of the secondary metallization layer when its thickness has reached about 90% of a radius of the nanospheres.

13. The method of claim 11 including:
    depositing a tertiary metallization layer on the secondary metallization layer to thereby form a metallization stack; and
    selectively etching the metallization stack to remove a portion of the secondary metallization layer to expose a greater surface area of the primary and tertiary metallization layers.

14. The method of claim 13 wherein the primary and tertiary metallization layers are have different widths in the etch metallization stack.

15. The method of claim 13 wherein the secondary metallization layer is gold.

16. The method of claim 13 including selecting the primary and tertiary metallization layers from the group consisting of platinum, iridium, iridium oxide, and titanium nitride.

* * * * *